US009670184B2

(12) United States Patent
Tan et al.

(10) Patent No.: US 9,670,184 B2
(45) Date of Patent: Jun. 6, 2017

(54) AMORPHOUS ALLISARTAN ISOPROXIL, PREPARATION METHOD THEREFOR, AND PHARMACEUTICAL COMPOSITION CONTAINING AMORPHOUS ALLISARTAN ISOPROXIL

(71) Applicant: SHENZHEN SALUBRIS PHARMACEUTICALS CO. LTD, Shenzhen (CN)

(72) Inventors: Duanming Tan, Shenzhen (CN); Jun Ou, Shenzhen (CN); Guanhao Ye, Shenzhen (CN); Shui Bu, Shenzhen (CN)

(73) Assignee: SHENZHEN SALUBRIS PHARMACEUTICALS CO. LTD, Shenzhen (CN)

( * ) Notice: Subject to any disclaimer, the term of this patent is extended or adjusted under 35 U.S.C. 154(b) by 0 days.

(21) Appl. No.: 15/032,532

(22) PCT Filed: Oct. 29, 2014

(86) PCT No.: PCT/CN2014/089775
§ 371 (c)(1),
(2) Date: Apr. 27, 2016

(87) PCT Pub. No.: WO2015/062498
PCT Pub. Date: May 7, 2015

(65) Prior Publication Data
US 2016/0251338 A1 Sep. 1, 2016

(30) Foreign Application Priority Data
Nov. 1, 2013 (CN) .......................... 2013 1 0535073

(51) Int. Cl.
C07D 403/10 (2006.01)
A61K 31/4178 (2006.01)

(52) U.S. Cl.
CPC ........ *C07D 403/10* (2013.01); *A61K 31/4178* (2013.01)

(58) Field of Classification Search
CPC .................................................. C07D 403/10
USPC ........................................................ 548/400
See application file for complete search history.

(56) References Cited

U.S. PATENT DOCUMENTS

| | | | |
|---|---|---|---|
| 2009/0326025 A1 | 12/2009 | Lu et al. | |
| 2010/0168193 A1 | 7/2010 | Guo | |
| 2010/0292286 A1 | 11/2010 | Guo et al. | |

FOREIGN PATENT DOCUMENTS

| | | |
|---|---|---|
| CN | 101317842 A | 12/2008 |
| CN | 101317842 A | 12/2008 |
| CN | 103965171 A | 8/2014 |
| CN | 103965171 A | 8/2014 |
| EP | 1988090 A1 | 11/2008 |
| EP | 2157089 A1 | 2/2010 |
| EP | 2213669 A1 | 8/2010 |

OTHER PUBLICATIONS

International Preliminary Report on Patentability in corresponding PCT Application No. PCT/CN2014/089775, mailed May 3, 2016.
International Search Report and Written Opinion in corresponding PCT Application No. PCT/CN2014/089775, mailed Feb. 3, 2015.
International Search Report in corresponding PCT Application No. PCT/CN2014/089775, mailed Feb. 3, 2015.
Shrawan Baghel, et al., "Polymeric Amorphous Solid Dispersions: A Review of Amorphization, Crystallization, Stabilization, Solid-State Characterization, and Aqueous Solubilization of Biopharmaceutical Classification System Class II Drugs", *Journal of Pharmaceutical Sciences*, 105 (2016), pp. 2527-2544.
Extended European Search Report for European Patent Application No. 14856893.4 issued on Mar. 15, 2017. 7 pages.
Hancock, B. C. et al. "What is the true solubility advantage for amorphous pharmaceuticals?" Pharmaceutical Research, Springer New York LLC, US, vol. 17, No. 4, Apr. 1, 2000 (Apr. 1, 2000). pp. 397-404. XP009086748, ISSN: 0724-8741. 8 pages

*Primary Examiner* — Kristin Vajda
(74) *Attorney, Agent, or Firm* — Leason Ellis LLP (57) ABSTRACT

The present invention relates to an amorphous allisartan isoproxil which is an angiotensin II receptor blocker with good flowability and a large bulk density and with no obvious electrostatic phenomenon; the find of the amorphous allisartan isoproxil can effectively reduce the generation of dust pollution during the production, thereby providing convenience the production of allisartan isoproxil. The present invention also relates to a pharmaceutical composition containing the amorphous allisartan isoproxil. The pharmaceutical composition is highly stable, and allisartan isoproxil formulation prepared from the pharmaceutical composition can effectively ensure the quality of the drug.

15 Claims, 5 Drawing Sheets

AMORPHOUS ALLISARTAN ISOPROXIL, PREPARATION METHOD THEREFOR, AND PHARMACEUTICAL COMPOSITION CONTAINING AMORPHOUS ALLISARTAN ISOPROXIL

CROSS-REFERENCE TO RELATED PATENT APPLICATIONS

This application is a U.S. National Phase Application under 35 U.S.C. §371 of International Patent Application No. PCT/CN2014/089775, filed Oct. 29, 2014, and claims the priority of Chinese Application No. 201310535073.6, filed Nov. 1, 2013, all of which are incorporated by reference in their entireties. The International Application was published on May 7, 2015 as International Publication No. WO 2015/062498 A1.

FIELD OF THE INVENTION

The present invention relates to the field of pharmaceutical chemistry, and particularly relates to amorphous allisartan isoproxil, preparation method thereof and pharmaceutical composition containing the amorphous allisartan isoproxil.

BACKGROUND OF THE INVENTION

Allisartan isoproxil (CAS: 947331-05-7) with the chemical name of 2-butyl-4-chloro-1-[2'-(1H-tetrazol-5-yl)-1,1'-biphenyl-methyl]-imidazole-5-carboxylic acid, 1-[(isopropoxy)-carbonyloxy]methyl ester, is a novel angiotensin II receptor antagonist. Chinese patent CN200680000397.8 disclosed the structural of allisartan isoproxil. Allisartan isoproxil shows low toxicity and superior antihypertensive efficacy compared with like products (e.g., losartan). Allisartan isoproxil exerts its antihypertensive effect by generating active metabolite (EXP3174).

Allisartan isoproxil

EXP3174

According to the prior art, allisartan isoproxil shows poor flowability, small bulk density, and obvious electrostatic phenomenon. Chinese patent CN200710094131.0 disclosed an allisartan isoproxil crystal form and preparation method thereof. The allisartan isoproxil crystal prepared with this method shows high stability, but relatively small bulk density, poor flowability, and obvious electrostatic phenomenon after drying. It causes dust pollution during the pulverizing, sub-packaging and using of this crystal, which on the one hand causes inconvenience for cleaning and labor protecting in operation site, and on the other hand causes inconvenience for weighing accuracy and packaging.

Chinese patents CN200710094021.4 and CN201110289695.6 both disclosed the preparation methods of allisartan isoproxil, and as repeated by the inventor, the resulted crystal forms are consistent with that disclosed in CN200710094131.0.

In view of the aforementioned disadvantages of allisartan isoproxil disclosed in the prior art, it can be seen that the technical problem to be addressed firstly in the present invention is to obtain allisartan isoproxil with flowability suits for subsequent producing, with appropriate bulk density and without obvious electrostatic phenomenon.

SUMMARY OF THE INVENTION

To address the disadvantages in the prior art, through a lot of experiments, the inventor obtained an improved allisartan isoproxil bulk drug, which shows better flowability than allisartan isoproxil crystal disclosed in the prior art, and more, the bulk density is obviously greater than allisartan isoproxil crystal disclosed in the prior art, and no obvious electrostatic phenomenon is observed. Through further analysis, it is found that the resulted allisartan isoproxil exists in amorphous form which has not been disclosed in the prior art, and more surprisingly, the resulted amorphous allisartan isoproxil can exist stably in pharmaceutical composition. The amorphous allisartan isoproxil in present invention not only addresses the disadvantages of the allisartan isoproxil crystal of the prior art, provides convenience for allisartan isoproxil preparation productions, but also provides more options for optimizing formulation of allisartan isoproxil.

Figure 1:
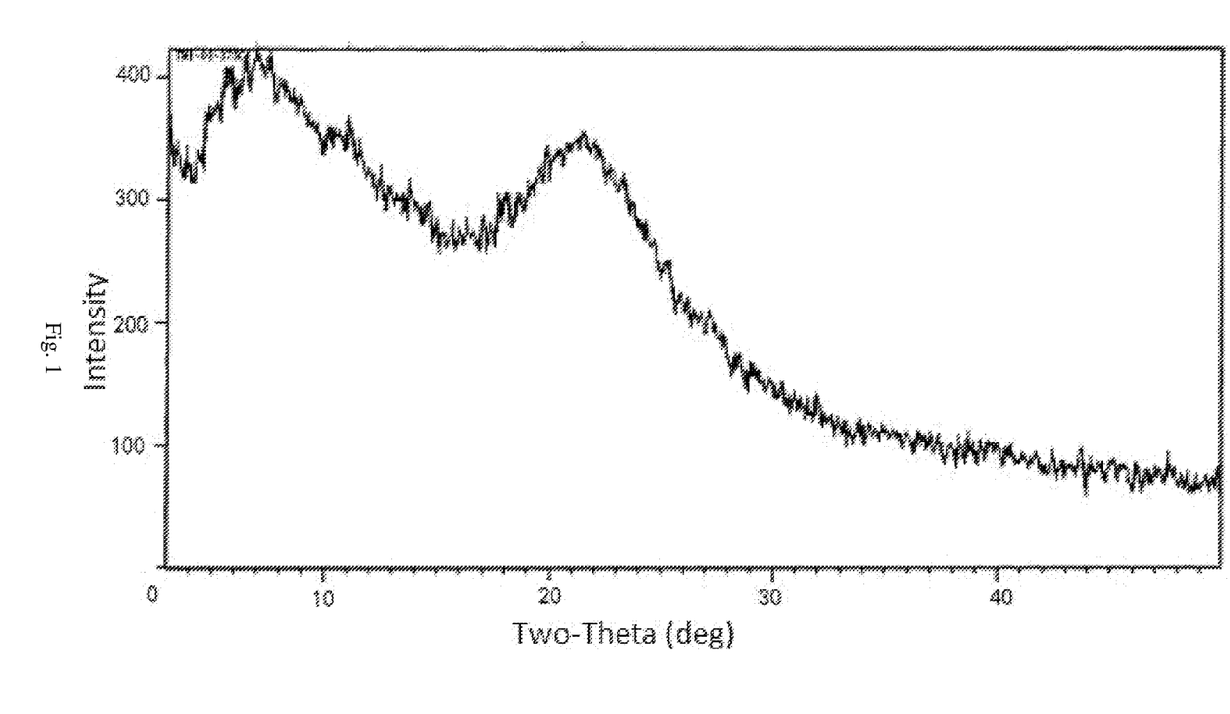
FIG. 1 is XRD spectrum of the amorphous allisartan isoproxil obtained from experiment 1.
Figure 2:
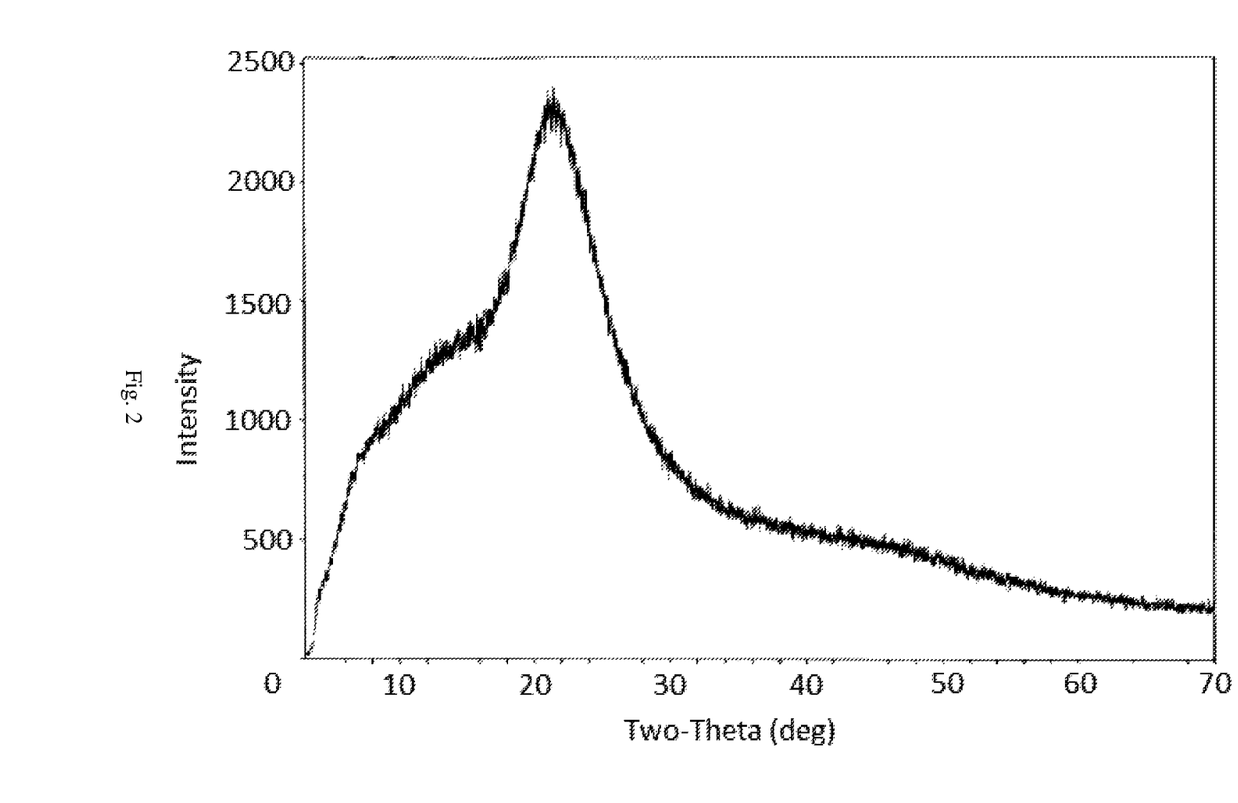
FIG. 2 is XRD spectrum of the amorphous allisartan isoproxil obtained from experiment 3.

The amorphous solid of the present invention has no obvious and sharp diffraction peak in X-ray powder diffraction (XRD) spectrum. As well-known in the art, compound in amorphous form is thermodynamic instability, which means molecules are completely disordered, and thus no diffraction peak or non-sharp diffraction peak/peaks are observed in XRD spectrum of amorphous form. In conclusion, compound without sharp diffraction peak in XRD spectrum can be defined as amorphous. In one embodiment of the present invention, the amorphous allisartan isoproxil do not have any obvious and sharp diffraction peak in the XRD spectrum, which can be defined as amorphous form. In one embodiment of the present invention, the amorphous allisartan isoproxil has non-sharp diffraction peak/peaks in the XRD spectrum. In one embodiment as shown in FIG. 1, XRD spectrum of amorphous allisartan isoproxil has two wide and weak non-sharp diffraction peaks when 2θ is between 0° and 30°; In one embodiment as shown in FIG. 2, XRD spectrum of amorphous allisartan isoproxil has one wide and weak non-sharp peak when 2θ is between 0° and 30° in the XRD spectrum. Furthermore, for FIG. 1, two wide and weak diffraction peaks respectively exist when 2θ is between 0° and 15° and when 2θ is between 15° and 30° in the XRD spectrum. Both FIGS. 1 and 2 demonstrate that the allisartan isoproxil provided by present invention exist in amorphous form.

Figure 3:
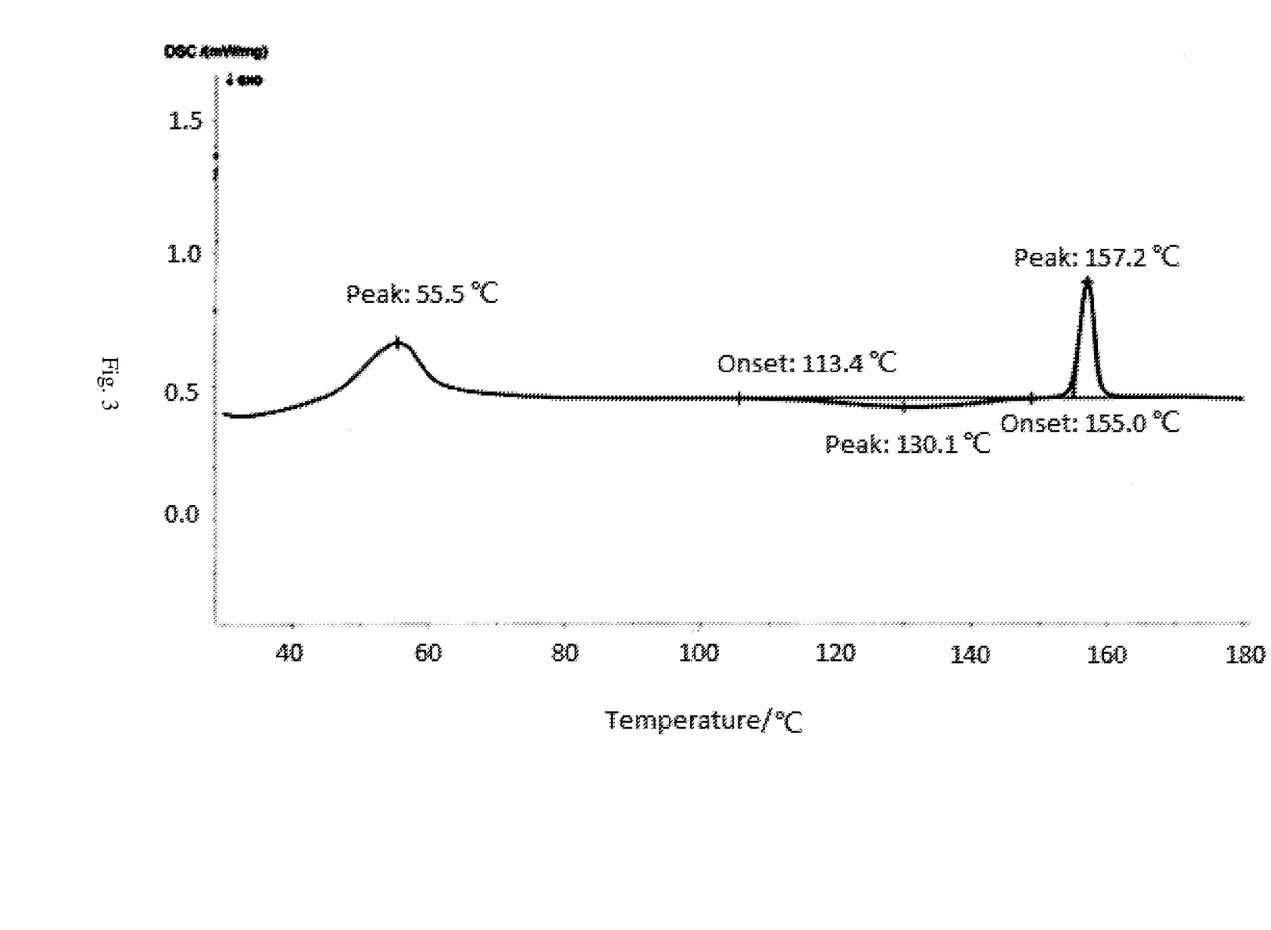
FIG. 3 is DSC spectrum of the amorphous allisartan isoproxil obtained from experiment 1.

The differential scanning calorimetry (DSC) spectrum of the amorphous allisartan isoproxil is as shown in FIG. 3. Particularly, the spectrum shows that: the amorphous form has an endothermic peak at 56±3° C., an exothermic peak at 130±3° C., and an endothermic peak at 157±3° C.

Figure 4:
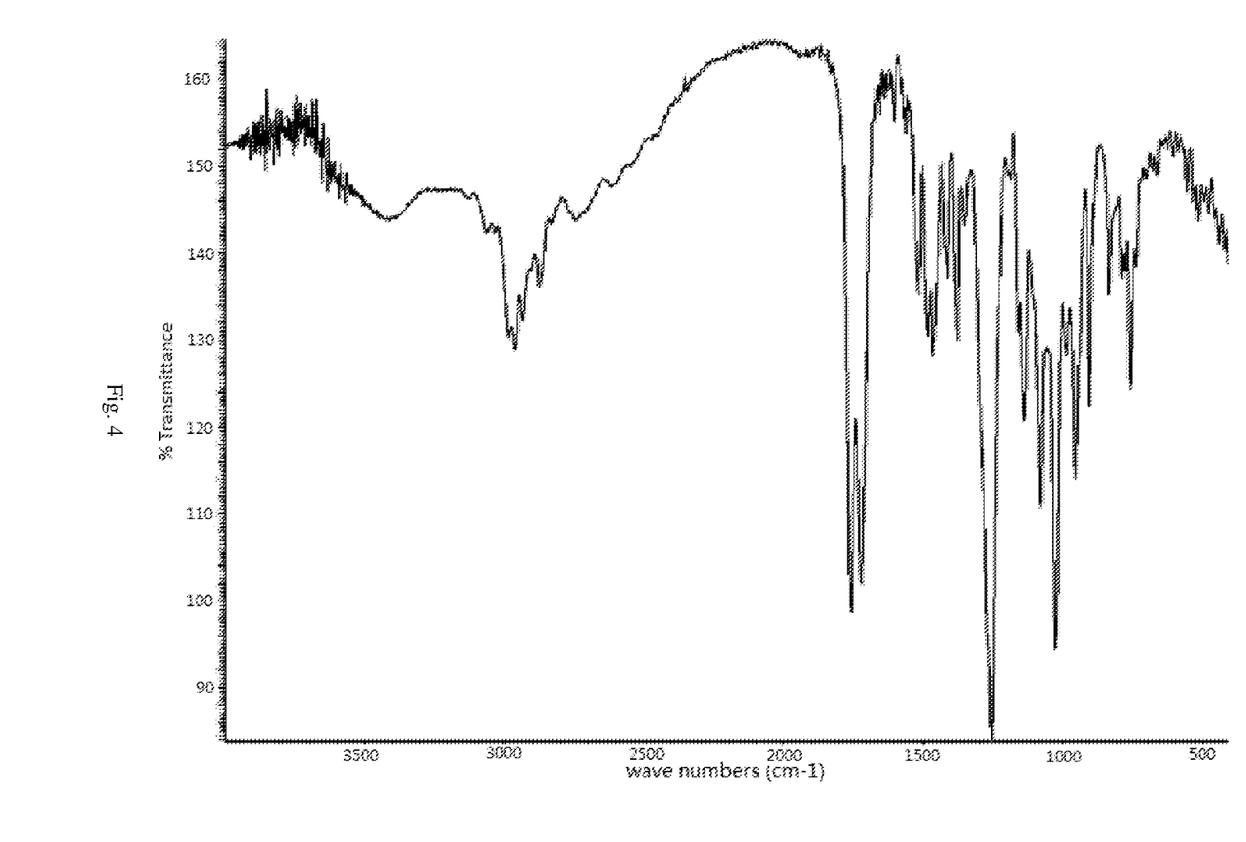
FIG. 4 is infrared spectrum of the amorphous allisartan isoproxil obtained from experiment 1.

The infrared (IR) spectrums of amorphous allisartan isoproxil is as shown in FIG. 4. Particularly, the amorphous allisartan isoproxil has absorption peaks near 2961, 1759, 1720, 1466, 1378, 1255, 1138, 1080, 1027, 955, 906 and 760 $cm^{-1}$.

Another object of the present invention is to provide a method capable of stably preparing the amorphous allisartan isoproxil of the present invention, and the method includes the following steps:
1) dissolving allisartan isoproxil crystal in an organic solvent at room temperature or under heating; and
2) concentrating the resulted solution under reduced pressure until it is dried, then drying in vacuum until the weight is constant and cooling to room temperature, so as to obtain amorphous allisartan isoproxil.

In step 1) the allisartan isoproxil crystal is preferably the crystal obtained by the method of patent CN200710094131.0, the organic solvent is dichloromethane or mixed dichloromethane-methanol solvent, and $V_{dichloromethane}:V_{methanol}=100:0-5$, the volume-mass ratio of organic solvent to allisartan isoproxil is controlled between 1.5-2 ml/g; if necessary, an appropriate amount of active carbon is added for decolorization; in step 2) the relative pressure used for concentration under reduced pressure is equal to or smaller than −0.05 MPa (≤−0.05 MPa), and the temperature is controlled at 0-40° C.; and the relative pressure of vacuum drying is equal to or smaller than −0.09 MPa (≤−0.09 MPa) and the temperature is at 30-50° C. More particularly, if amorphous allisartan isoproxil as shown in FIG. 1 is expected, lower slurry temperature or lower relative pressure is needed during concentration, in one embodiment, at relative pressure of −0.05 MPa and temperature of 25° C., in another embodiment, at relative pressure of −0.09 MPa and temperature of 40° C. If amorphous allisartan isoproxil as shown in FIG. 2 is expected, higher relative pressure and higher slurry temperature are needed during concentration, in one embodiment, at relative pressure of −0.05 MPa and temperature of 40° C.

Various technical parameters of the preparation method (e.g., the solvent proportion, temperature, relative pressure, etc.) are keys for stably obtaining the amorphous allisartan isoproxil of present invention, and variations of technical parameters may lead to different experiment results. For example, it is found through comparative experiments that: on the premise other conditions are not changed, when a mixed dichloromethane-methanol solvent with the ratio of $V_{dichloromethane}:V_{methanol}=100:10$ is used, the resulted allisartan isoproxil is crystal form disclosed in the prior art.

Through experiments, the inventor finds that the bulk density of amorphous allisartan isoproxil powder of the present invention is significantly is greater than that of crystal powder in the prior art, and also finds that the electrostatic phenomenon of the amorphous powder is significantly reduced. Additionally, the flowability of the amorphous powder is also significantly better than that of the crystal powder disclosed in the prior art. The use of the amorphous allisartan isoproxil can not only greatly reduce the dust pollution during production, but also provide convenience for the subsequent processes of allisartan isoproxil production.

A further object of the present invention is to providing a pharmaceutical composition containing the amorphous allisartan isoproxil of the present invention.

The pharmaceutical composition is composed of the amorphous allisartan isoproxil of the present invention and pharmaceutic excipients. Particularly, the pharmaceutic excipients include but not limited to fillers, binders, disintegrants and lubricants.

The pharmaceutical composition can be prepared into formulations which include but not limited to tablets, capsules, granules, powders, suppositories and the like. Preferably, the pharmaceutical composition can be prepared into tablets.

The pharmaceutic excipients are those commonly used in the art. Particularly, the fillers include but not limited to starch, lactose, mannitol, sucrose, microcrystalline cellulose and the like; the binders include but not limited to hydroxymethylcellulose, sodium carboxymethylcellulose, starch slurry, gelatin and the like; the disintegrants include but not limited to crospovidone, calcium carbonate, sodium carbonate, potato starch or tapioca starch, compound silicate, alginic acid and the like; and the lubricants include but not limited to aerosil, talcum powder, magnesium stearate, solid polyethylene glycol, sodium lauryl sulfate and the like, and if desired, a further coating process can be introduced on the formulation with coating materials in the art. The amorphous allisartan isoproxil of the present invention can stably exists in the pharmaceutical composition. Particularly, by analyzing the tablet prepared through conventional methods in the art, it is found through XRD detection that, after being stored for 6 months under accelerated stability conditions (40° C./75% RH), allisartan isoproxil still exist in the same amorphous form and with substantially constant content, thereby demonstrate the quality of the formulation can be well ensured.

In one embodiment, the ingredients of the allisartan isoproxil pharmaceutical composition is as follows:

| | Ingredients | Tablet Composition (mg/tablet) | Mass Percent |
|---|---|---|---|
| Bulk Drug | Allisartan isoproxil | 240.0 | 48.0% |
| Internal Excipient | crospovidone | 25.0 | 5.0% |
| | microcrystalline cellulose | 48.0 | 9.6% |
| | lactose | 113.0 | 22.6% |
| | aerosil | 3.5 | 0.7% |
| | magnesium stearate | 3.5 | 0.7% |
| External | crospovidone | 50.0 | 10.0% |

| | Ingredients | Tablet Composition (mg/tablet) | Mass Percent |
|---|---|---|---|
| Excipient | aerosil | 2.5 | 0.5% |
| | magnesium stearate | 2.5 | 0.5% |
| Coating Material | gastric-soluble film-coating premixed agent | 12.0 | 2.4% |
| Total | | 500.0 | 100.0% |

Mixing the bulk drug and internal excipients uniformly in sequence according to the proportions listed above, then pelletizing via dry granulating method to obtain internal-phase granules; adding and mixing external excipients sequentially according to the proportions listed above to obtain the pharmaceutical composition; compressing the resulted pharmaceutical composition, and the resulted tablets are coated.

Through analysis, it is found that the amorphous allisartan isoproxil can exist stably in tablets resulted above. Particularly, it is found from the powder X-ray diffraction spectrum of the resulted tablets that the allisartan isoproxil still exists as amorphous form, and remains stable as the same amorphous form after being stored for long period of time.

Through experiments, the inventor finds that the amorphous allisartan isoproxil provided by the present invention can stably exist in the pharmaceutical composition, and thus if it is demonstrated through detection methods that the active ingredient exists as amorphous form in the formulation product, then it should be considered that the amorphous allisartan isoproxil provided by the present invention is used. In addition to X-ray powder diffraction (XRD), further detection methods include the differential scanning calorimetry (DSC), the infrared (IR) spectrometry, the Raman spectroscopy (Raman), the solid-state nuclear magnetic resonance spectroscopy (SSNMR), and other detection methods which can demonstrate the form that allisartan isoproxil exists in the pharmaceutical composition.

Compared with the prior art, the present invention shows following advantages and beneficial effects:
1. Providing an amorphous allisartan isoproxil not disclosed in the prior art, whose bulk density is greater than that of the crystal disclosed in the prior art, electrostatic phenomenon is not obvious, and flowability is obviously better than that of the crystal disclosed in the prior art.
2. Providing a preparation method of the allisartan isoproxil, which can prepare the desired amorphous allisartan isoproxil stably.
3. Providing a pharmaceutical composition containing the amorphous allisartan isoproxil of the present invention.

DETAILED DESCRIPTION OF THE EXPERIMENTS

All of the detection data and spectrums of the present invention are obtained by conventional analytical instruments in conventional methods under conventional detect conditions in the art, the present invention is further exemplarily described in details in conjunction with experiments and figures, although the implementation of the present invention is not limited thereto.

The XRD spectrum as shown in FIG. 1 of the present invention is obtained by detecting with Empyrean X-ray diffractometer under the following detection conditions: Cu Kα1, a voltage of 40 kV, a current of 40 mA, a divergence slit of ⅛₃₂°, a scattering slit of ⅟₁₆°, an antiscattering slit of 7.5 mm, a 2θ range of 3-50°, a step size of 0.02°, and time per step of 40 s.

The XRD spectrum as shown in FIG. 2 of the present invention is obtained by detecting with a Rigaku MiniFlex 600 X-ray diffractometer under the following detection conditions: Cu Kα1, a voltage of 40 kV; a current of 15 mA; a slit of Soller (inc.) 2.5 deg, IHS 10.0 mm, DS 0.625 deg, SS 13.0 mm and Soller (rec.) 2.5 deg; a scattering slit of ⅟₁₆°, an antiscattering slit of 7.5 mm, a 2θ range of 3-70°, a step size of 0.02°, and 5 steps/min.

The DSC spectrum of the present invention is obtained by detection with the DSC 204F1 differential scanning calorimeter from Netzsch Corporation under $N_2$ atmosphere (with a purity of more than or equal to 99.99%, 20 ml/min), wherein the heating curve is recorded from room temperature to 180° C., with a temperature rising rate of 10° C./min.

The infrared spectrum of the present invention is obtained by using KBr pellet method.

Experiment 1

16.5 ml dichloromethane was added into a flask containing 10 g allisartan isoproxil crystal, and the flask was heated to reflux until the solution became clear. After the solvent was removed by concentrating the solution at a relative pressure of −0.05 MPa and 25° C., the obtained solid was dried in vacuum at a relative pressure of −0.09 MPa and 40° C. until the weight thereof was constant, and then cooled to room temperature to obtain the amorphous allisartan isoproxil. The resulted amorphous allisartan isoproxil showed no obvious electrostatic phenomenon. The XRD spectrum was shown as FIG. 1, the DSC spectrum was shown as FIG. 3, and the IR spectrum was shown as FIG. 4.

Experiment 2

20 ml mixed dichloromethane/methanol solution ($V_{dichloromethane}:V_{methanol}$=100:5) was added into a flask containing 10 g allisartan isoproxil crystal, and the flask was heated to reflux until the solution became clear. After the solvent was removed by concentrating the solution in water bath at a relative pressure of −0.09 MPa and 40° C., the obtained solid was dried in vacuum at a relative pressure of −0.095 MPa and 50° C. until the weight thereof was constant, and then cooled to room temperature to obtain the same amorphous allisartan isoproxil as experiment 1. The resulted amorphous allisartan isoproxil showed no obvious electrostatic phenomenon.

Experiment 3

16.5 ml dichloromethane was added into a flask containing 10 g allisartan isoproxil crystal, and the flask was heated to reflux until the solution become clear. After the solvent was removed by concentrating the solution at a relative pressure of −0.05 MPa and 40° C., the obtained solid was dried in vacuum at a relative pressure of −0.09 MPa and 50° C. until the weight thereof was constant, and then cooled to room temperature to obtain the amorphous allisartan isoproxil. The XRD spectrum was shown as FIG. 2 and the IR spectrum was shown as FIG. 4. The resulted amorphous allisartan isoproxil showed no obvious electrostatic phenomenon.

Experiment 4

20 ml mixed dichloromethane/methanol solution ($V_{dichloromethane}:V_{methanol}=100:10$) was added into a flask containing 10 g allisartan isoproxil crystal, and the flask was heated to reflux until the solution became clear. Then the solid was obtained by the operation according to the conditions of experiment 2 so as to obtain an allisartan isoproxil crystal with a melting point of 156-157° C.

Experiment 5

Fine and loose crystal powders (referred to as "patent crystal") were obtained according to the method disclosed in patent CN200710094131.0, which showed obvious electrostatic phenomenon after drying. The powders of experiment 1 and 3 were pulverized and then sieved through a 100-mesh screen to obtain powders with particle size similar to the crystal powder. Then the repose angles of the powders were detected respectively by using a fixed-funnel method; and the bulk densities of the powders were detected respectively by using measurement in a graduated cylinder (Method I of Bulk Density disclosed in Ph. Eur), and the results were shown in the table below:

| Sample | Repose Angle (°) | Bulk Density (g/ml) |
| --- | --- | --- |
| Amorphous allisartan isoproxil obtained from experiment 1 | 33-36 | 0.77 |
| Amorphous allisartan isoproxil obtained from experiment 3 | 33-36 | 0.79 |
| Patent Crystal | 48-53 | 0.51 |

It could be seen from the aforementioned data that compared with the crystal obtained according to patent CN200710094131.0, the amorphous allisartan isoproxil prepared according to the present invention showed smaller repose angle and greater bulk density, and thus the amorphous allisartan isoproxil provided by the present invention showed better flowability.

Experiment 6

A pharmaceutical composition was prepared by using the amorphous allisartan isoproxil obtained according to the method of experiment 1 as the bulk drug, and further prepared as tablets, with the ingredients as follows:

| | Ingredients | Tablet Composition (g) |
| --- | --- | --- |
| Bulk Drug | Allisartan isoproxil | 240.0 |
| Internal | crospovidone | 25.0 |

-continued

| | Ingredients | Tablet Composition (g) |
| --- | --- | --- |
| Excipient | microcrystalline cellulose | 48.0 |
| | lactose | 113.0 |
| | aerosil | 3.5 |
| | magnesium stearate | 3.5 |
| External Excipient | crospovidone | 50.0 |
| | aerosil | 2.5 |
| | magnesium stearate | 2.5 |
| Coating Material | gastric-soluble film-coating premixed agent | 12.0 |
| Total | | 500.0 1000 pieces of tablets |

Mixing the Bulk drug and internal excipients uniformly in sequence according to the proportions listed above, then pelletizing via dry granulating method to obtain internal-phase granules; adding and mixing external excipients sequentially according to the proportions listed above to obtain the pharmaceutical composition; compressing the resulted pharmaceutical composition, and the resulted tablets are coated.

Figure 5:
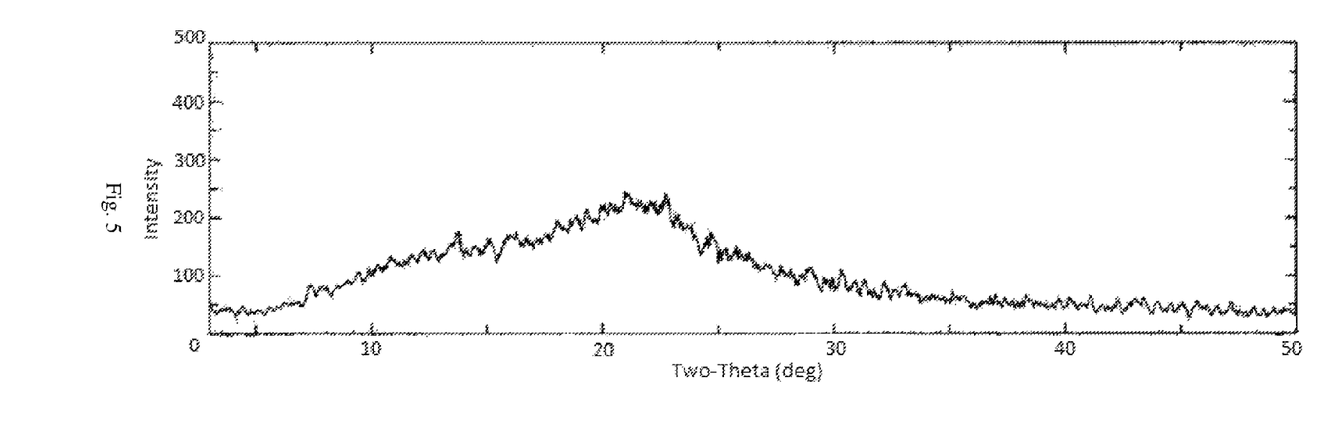
FIG. 5 is XRD spectrum of the pharmaceutical composition obtained from experiment 5.

Detecting the obtained tablets, the resulted XRD spectrum was as shown in FIG. 5, which showed that the active ingredient still existed as amorphous form in tablets. After being stored under conditions of 40° C./75% RH for 6 months, the active ingredient was detected to exist as the same amorphous form with a substantially constant content through XRD.

Similarly, the pharmaceutical composition was prepared by using the amorphous allisartan isoproxil obtained according to the method of experiment 3 as bulk drug, and the active ingredient contained in the obtained tablets that further prepared showed stability consistent with that of the aforementioned tablets.

The aforementioned experiments are preferred implementations of the present invention, although the implementation of the present invention is not limited thereto. Any other change, modification, substitution, combination or simplification without departing from the spirit essence and principle of the present invention are deemed to be equivalent modes that falling into the protection scope of the present invention.

The invention claimed is:

1. An amorphous allisartan isoproxil, wherein the amorphous allisartan isoproxil has no sharp diffraction peak in an X-ray diffraction (XRD) spectrum.

2. The amorphous allisartan isoproxil of claim 1, wherein the amorphous allisartan isoproxil has non-sharp diffraction peak or peaks XRD spectrum.

3. The amorphous allisartan isoproxil of claim 1, wherein the amorphous allisartan isoproxil has two wide and weak diffraction peaks in the XRD spectrum of the amorphous allisartan isoproxil, and wherein 2θ is between 0° and 30°.

4. The amorphous allisartan isoproxil of any of claim 1, wherein the amorphous allisartan isoproxil has an XRD spectrum as shown in FIG. 1.

5. The amorphous allisartan isoproxil of claim 1, wherein the amorphous allisartan isoproxil has an endothermic peak at 56±3° C., an exothermic peak at 130±3° C., and an endothermic peak at 157±3° C. in a differential scanning calorimetry (DSC) spectrum.

6. The amorphous allisartan isoproxil of claim 1, wherein the amorphous allisartan isoproxil has a DSC spectrum as shown in FIG. 2.

7. The amorphous allisartan isoproxil of claim 1, wherein the amorphous allisartan isoproxil has a wide and weak diffraction peak in the XRD spectrum, and wherein 2θ is between 0° and 30°.

8. The amorphous allisartan isoproxil of claim 1, wherein the amorphous allisartan isoproxil has an XRD spectrum as shown in FIG. 2.

9. The amorphous allisartan isoproxil of claim 1, wherein the infrared spectrum of the amorphous allisartan isoproxil has absorption peaks at 2961, 1759, 1720, 1466, 1378, 1255, 1138, 1080, 1027, 955, 906 and 760 cm$^{-1}$.

10. A method for preparing the amorphous allisartan isoproxil of claim 1, wherein the method comprises the following steps:
   1) dissolving crystalline allisartan isoproxil in an organic solvent at room temperature or under heat to obtain a solution;
   2) concentrating the solution under reduced pressure to obtain a solid,
   3) drying the solid under vacuum, and
   4) cooling the dried solid to room temperature, so as to obtain amorphous allisartan isoproxil, wherein in step 1) the organic solvent is dichloromethane or a mixed dichloromethane-methanol solvent, and $V_{dichloromethane}:V_{methanol}=100:0\text{-}5$, the volume-mass ratio of an organic solvent to allisartan isoproxil is controlled at 1.5-2 ml/g; wherein in step 2) the relative pressure used for concentration under reduced pressure is equal to or smaller than −0.05 MPa, and the temperature is 0-40° C.; and wherein in step 3) the relative pressure of drying under vacuum is equal to or smaller than −0.09 MPa and the temperature is 30-50° C.

11. The method of claim 10, wherein in step 2) the relative pressure is −0.05 MPa and the temperature is 25° C.; or the relative pressure is −0.09 MPa and the temperature is 40° C.

12. The method of claim 10, wherein in step 2) the relative pressure is −0.05 MPa and the temperature is 40° C.

13. The method of claim 10, wherein the crystalline allisartan isoproxil of step 1) is obtained according to a process comprising:
   (a) dissolving allisartan isoproxil in a polar solvent at a first temperature ranging from about 10° C. to about the boiling point of the solvent to obtain a solution, wherein the polar solvent is selected from the group consisting of ethanol, isopropanol, acetonitrile, acetone, ethyl acetate, dioxane, and mixtures thereof,
   (b) cooling the solution to a second temperature ranging from about −25° C. to about 25° C., and
   (c) precipitating allisartan isoproxil to obtain crystalline allisartan isoproxil.

14. An allisartan isoproxil pharmaceutical composition, comprising the amorphous allisartan isoproxil of claim 1.

15. An allisartan isoproxil tablet, wherein the allisartan isoproxil tablet is prepared from the allisartan isoproxil pharmaceutical composition of claim 14.

* * * * *